United States Patent [19]

Galardy et al.

[11] Patent Number: 4,558,034

[45] Date of Patent: Dec. 10, 1985

[54] INHIBITORS OF BACTERIAL COLLAGENASE

[75] Inventors: Richard E. Galardy; Damian Grobelny, both of Lexington, Ky.

[73] Assignee: The Board of Trustees of the University of Kentucky, Lexington, Ky.

[21] Appl. No.: 576,005

[22] Filed: Jan. 31, 1984

[51] Int. Cl.$^4$ .................... A61K 37/00; C07C 103/52
[52] U.S. Cl. .................................. 514/7; 260/112.5 R
[58] Field of Search ................. 424/177; 260/112.5 R; 514/7

[56] References Cited

U.S. PATENT DOCUMENTS

| | | | |
|---|---|---|---|
| 4,100,275 | 7/1978 | Atherton et al. | 424/211 |
| 4,263,293 | 4/1981 | Sundeen et al. | 424/248.5 |
| 4,276,284 | 6/1981 | Brown | 424/101 |
| 4,316,896 | 2/1982 | Thorsett et al. | 424/200 |
| 4,361,574 | 11/1982 | Grant et al. | 424/270 |
| 4,379,146 | 4/1983 | Greenlee et al. | 424/177 |
| 4,432,971 | 2/1984 | Karanewsky . | |
| 4,432,972 | 2/1984 | Karanewsky . | |
| 4,442,089 | 4/1984 | Horovitz . | |

OTHER PUBLICATIONS

Chem. Abstr., vol. 95, (1981) 25603y.
Proc. Natl. Acad. Sci., vol. 79, pp. 2176–2180, Apr. 1982.
Galardy, Richard, "Inhibition of Angiotensin Converting Enzyme with N$^\alpha$-Phosphoryl-L-Ananyl-L-Proline and N$^\alpha$-Phosphoryl-L-Valyl-L-Tryptophan", *Biochemical and Biophysical Research Communications*, vol. 97, pp. 94–99 (1980).
Galardy et al., "Inhibition of Collagenase from *Clostridum histolyticum* by Phosphoric and Phosphonic Amides", American Chemical Society, *Biochemistry*, vol. 22, pp. 4561–4567 (1983).

*Primary Examiner*—Delbert R. Phillips
*Attorney, Agent, or Firm*—Lowe, King, Price & Becker

[57] ABSTRACT

This invention relates to amino acid derivatives that are useful as inhibitors of bacterial collagenase. The compounds of this invention have a general formula:

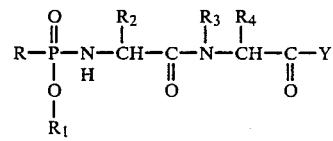

wherein R is alkyl, aralkyl, aryl, alkoxy, aryloxy, hydroxy or pharmaceutically acceptable salts thereof; $R_1$ is hydrogen, alkali metal, lower alkyl, phenyl lower alkyl, or phenyl, or substituted phenyl wherein the substituent is halo, lower alkoxy or lower alkyl or nitro or carboxy or cyano, and pharmaceutically acceptable salts thereof; $R_2$, $R_3$ and $R_4$ is hydrogen or alkyl; $R_2$ and $R_4$ may be the side groups found on the 20 common $\alpha$-amino acids; $R_3$ and $R_4$ may be connected together to form an alkylene bridge of from 2 to 4 carbon atoms; Y is alkoxy, aryloxy, primary amide, amino acid derivative or

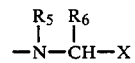

where $R_5$ and $R_6$ is hydrogen or alkyl; $R_5$ and $R_6$ may be connected together to form an alkylene bridge of from 2 to 4 carbon atoms; X is hydroxyl or pharmaceutically acceptable salts thereof, or an amino acid derivative.

11 Claims, No Drawings

INHIBITORS OF BACTERIAL COLLAGENASE

FIELD OF THE INVENTION

This invention relates to inhibitors of bacterial collagenase, and more particularly to amino acid derivatives useful for such purposes.

BACKGROUND OF THE INVENTION

Collagen is the major extracellular structural protein in skin, tendon, bone, cartilage, and connective tissue in vertebrates. Collagen fibrils form a structural matrix that binds groups of cells together to form tissues. Collagen constitutes about 40 percent of all proteins in the body. Once collagen fibers are formed, they are not renewed. Thus, although these fibers undergo certain changes as skin, muscles, bones, joints, blood vessels, etc. experience natural processes such as aging; these altered collagen fibrils are not repaired or replaced.

Collagen disease is any one of a group of pathological conditions that are clinically distinct and of various etiologies. They cause in common, however, wide spread and systemic pathologic changes in connective tissue formed by collagen. Such diseases include *lupus erythematosus*, dermatomyositis, scleroderma, *polyarteritis nodosa*, *thrombotic purpura*, rheumatic fever, and rheumatoid arthritis. Collagen pathology may be mediated by collagenase, an enzyme that degrades collagen.

Collagen exists in vivo in the form of a polypeptide chain composed of three helical subunits wound about a common axis. These molecules polymerize into insoluble fibrils, and exist in tissue in this form. The helical structure is resistant to attack by proteolytic, or digestive, enzymes that degrade less-resistant proteins. There are, however, natural enzymes including animal collagenases which are capable of cleaving and thereby breaking down collagen molecules.

It has been shown, for example, that collagenase is responsible for ulcers appearing after the eye has been burned with alkali; collagen comprises the major organic component of the cornea. Similarly, this relationship exists for other ulcerative conditions of the cornea, including viral ulcers, such as herpes simplex, vaccinia; bacterial ulcers; degenerative ulcers and ulcers of unknown origin.

In mammals, collagenase is one of the key enzymes involved in the joint and cartilage destruction of rheumatoid arthritis; see for example, *Arthritis And Rheumatism*, 20 (6): 1231 (1977). The action of mammalian collagenase has also been implicated as a causative factor in several other diseases in mammals. These diseases include periodontal disease, tumor invasiveness, and epidermolysis bullosa; see for example, *American Journal of Pathology*, 92 (2): 509 (1978) and *The New England Journal of Medicine*, 291(13):652 (1974).

Certain of the collagen disorders are bacterially mediated. Corneal melting during bacterial infections is believed to be caused, in part or in whole, by the digestion of corneal collagen due to bacterial collagenase. Current treatment involves the use of cysteine which is only a weak inhibitor of collagenase. Gangrene is commonly caused by Clostridium and bacterial collagenase is thought to be important in the progression and consequences of this infection. Thus, pharmaceutical compositions effective to inhibit bacterial collagenase would be useful in preventing or ameliorating certain diseases.

Additionally, a standard laboratory technique involves the use of commercially-produced bacterial collagenase to prepare dispersions of cells separated from various minced tissue samples. The use of collagenase inhibitors in vitro is necessary to stop the action of collagenase once sufficient numbers of cells have been released into suspension. Also, affinity column chromatography using a bound collagenase inhibitor may be utilized in the purification of collagenase. Thus, effective collagenase inhibitors have several uses beyond that of clinical pharmacology.

Accordingly, collagenase inhibitors are generally useful in ameliorating or preventing pathological conditions in which collagenases play an etiological role.

U.S. Pat. No. 4,263,293 to Sundeen et al discloses a mammalian collagenase inhibitor having the general formula:

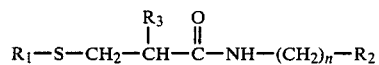

wherein $R_1$ is hydrogen, alkanoyl of 2 to 10 carbon atoms or arylcarbonyl; $R_2$ is 1-pyrrolidinyl, 1-piperidinyl, 4-morpholinyl, 1-piperazinyl, or 4-alkyl-1-piperazinyl; $R_3$ is alkyl of 3 to 8 carbon atoms, cycloalkyl, aryl, or arylalkyl; and n is an integer of 1 to 20. This patent discloses the use of certain compositions for the treatment of rheumatoid arthritis using these compounds, and provides methods for their preparation.

U.S. Pat. No. 4,361,574 to Grant et al also discloses a mammalian collagenase inhibitor in the form of a polyheterocyclic compound having the general formula:

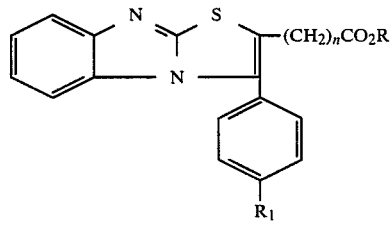

wherein R is hydrogen or lower alkyl, $R_1$ is hydrogen, lower alkyl, lower alkoxy, trifluoromethyl or halo; and n is 1. These compounds and methods for their preparation are also disclosed in U.S. Pat. Nos. 4,214,089, and 3,704,239.

Certain ulcers and other pathologic conditions involving tissue destruction have been treated by the application of a collagenase inhibitor; such as, cysteine, acetyl cysteine, ethylene diamine tetraacetic acid (or its sodium or calcium salts) and heparin. As taught by U.S. Pat. No. 4,276,284 to Brown, applications repeated daily over a course of time are effective in preventing or reducing ulceration.

Thorsett et al in U.S. Pat. No. 4,316,896 disclose converting enzyme inhibitors and antihypertensive amino acid derivatives of the formula:

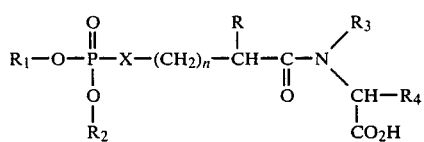

wherein n is 0 or 1; R is hydrogen, lower alkyl, phenyl lower alkyl, hydroxy phenyl lower alkyl, hydroxy lower alkyl, aminolower alkyl, guanidino lower alkyl, imidazoyl lower alkyl, indolyl lower alkyl, mercapto lower alkyl, lower alkyl mercapto lower alkyl; $R_3$ is hydrogen; $R_4$ is hydrogen, lower alkyl, phenyl lower alkyl, hydroxy phenyl lower alkyl, hydroxy lower alkyl, amino lower alkyl, guanidino lower alkyl, imidazoyl lower alkyl, indolyl lower alkyl, mercapto lower alkyl, lower alkyl mercapto lower alkyl; $R_3$ and $R_4$ may be connected together to form an alkylene bridge of from 2 to 4 carbon atoms or an alkylene bridge of from 2 to 3 carbon atoms and one sulfur atom; X is O, $NR^5$, S where $R_5=H$ or lower alkyl; $R_1$ is hydrogen, lower alkyl, aralkyl or aryl; and $R_2$ is hydrogen, lower alkyl, aralkyl or aryl and pharmaceutically acceptable salts thereof.

U.S. Pat. No. 4,379,146 to Greenlee et al discloses a substituted phosphonamide and related compounds useful as converting enzyme inhibitors and as antihypertensives. Compounds are disclosed of the general formula:

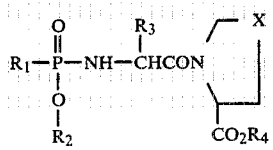

wherein $R_1$ is alkyl or substituted alkyl of $C_1-C_6$ wherein the substituent is halo, amino, acylamino; aralkyl wherein the alkyl is $C_1-C_4$ optionally substituted by amino or acylamino and wherein the aryl function is phenyl or naphthyl optionally substituted by halo or hydroxyl; or, heteroaralkyl wherein the alkyl is $C_1-C_4$ optionally substituted by amino or acylamino and wherein the heteroaryl group can be indolyl or thienyl; $R_2$ is H, lower alkyl of $C_1-C_4$, aralkyl such as benzyl; $R_3$ is lower alkyl of $C_1-C_6$ optionally substituted by an amino group; $R_4$ is H, lower alkyl of $C_1-C_6$, aralkyl such as benzyl; and X is $(CH_2)_n$ wherein n is 1 or 2, $CH-OCH_3$, $CH-OH$, or S. Other phosphonamides are taught by U.S. Pat. Nos. 4,100,275; 4,143,134; and 4,316,896.

SUMMARY OF THE INVENTION

In a composition aspect, the present invention refers to a bacterial collagenase inhibitor that is an amino acid derivative of the general formula

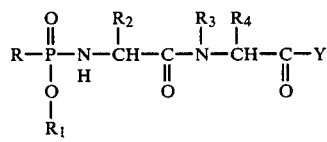

wherein R is alkyl, aralkyl, aryl, alkoxy, aryloxy, hydroxy or pharmaceutically acceptable salts thereof; $R_1$ is hydrogen, alkali metal, lower alkyl, phenyl lower alkyl, or phenyl, or substituted phenyl wherein the substituent is halo, lower alkoxy or lower alkyl or nitro or carboxy or cyano, and pharmaceutically acceptable salts thereof; $R_2$, $R_3$ and $R_4$ is hydrogen or alkyl; $R_2$ and $R_4$ may be the side groups found on the 20 common α-amino acids; $R_3$ and $R_4$ may be connected together to form an alkylene bridge of from 2 to 4 carbon atoms; Y is alkoxy, aryloxy, primary amide, amino acid derivative or

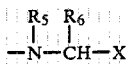

where $R_5$ and $R_6$ is hydrogen or alkyl; $R_5$ and $R_6$ may be connected together to form an alkylene bridge of from 2 to 4 carbon atoms; and X is hydroxyl or pharmaceutically acceptable salts thereof, or an amino acid derivative.

In a further composition aspect, this invention relates to pharmaceutical compositions wherein the compounds disclosed above comprise the effective ingredient. In a method of use aspect, the present invention relates to the use of compounds as disclosed above for the in vivo inhibition of bacterially produced collagenase.

Further aspects of the present invention relate to the use of the above-disclosed compounds as a ligand for chromatographic packing materials, and as a collagenase inhibitor in the preparation of cell dispersions.

DETAILED DESCRIPTION OF THE INVENTION

Bacterial collagenase is inhibited by amino acid derivatives of the general formula I

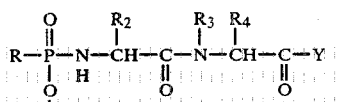

wherein R is alkyl, aralkyl, aryl, alkoxy, aryloxy, hydroxy or pharmaceutically acceptable salts thereof; $R_1$ is hydrogen, alkali metal, lower alkyl, phenyl lower alkyl, or phenyl, or substituted phenyl wherein the substituent is halo, lower alkoxy or lower alkyl or nitro or carboxy or cyano, and pharmaceutically acceptable salts thereof; $R_2$, $R_3$ and $R_4$ is hydrogen or alkyl; $R_2$ and $R_4$ may be the side groups found on the 20 common α-amino acids; $R_3$ and $R_4$ may also be connected together to form an alkylene bridge of from 2 to 4 carbon atoms; Y is alkoxy, aryloxy, primary amide, amino acid derivative or

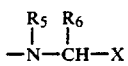

where $R_5$ and $R_6$ is hydrogen or alkyl; $R_5$ and $R_6$ may be connected together to form an alkylene bridge of from 2 to 4 carbon atoms; and X is hydroxyl or pharmaceutically acceptable salts thereof, or an amino acid derivative.

The term "lower alkyl" when used herein and in the appended claims includes straight and branched chain hydrocarbon radicals having from 1 to about 6 carbon atoms. Illustrative examples of which are methyl, ethyl, n-propyl, isopropyl, n-butyl, t-butyl, n-pentyl, isopentyl (isoamyl), n-hexyl, 3-methyl pentyl, 2,3-dimethyl butyl, etc. The term "aryl" includes both carbocyclic and heterocyclic (that is, containing one or more O, S, and N atoms as ring members) aromatic ring systems which may be substituted, for example, with one or more of halogen, fluorine, chlorine, bromine or iodine, trifluoromethyl, lower alkyl, lower alkoxy, lower alkanoyloxy, carbonyloxyalkyl, nitro, and cyano. Illustrative aromatic ring systems are phenyl, napthyl, furyl, thienyl, pyrolyl, immidazolyl, pyridyl, pyrimidinyl, indolyl, quinolyl, oxazolyl, and isooxazolyl. Lower alkoxy is a lower alkyl as defined above linked by an ether oxygen atom. Examples of lower alkoxy groups are methoxy, ethoxy, n-propoxy, n-butoxy, isopropoxy, tert-butoxy and so forth. The term "pharmacologically acceptable salt" contemplates the usual and customary forms of medicaments formulated in a solid or oral dosage form for pharmacological purposes. It also includes those employed to formulate either in unit dose or multidose form, oral and injectable suspensions and solutions, either directly or for reconstitution before administration.

The compounds of this invention can be utilized to block the action of collagenase of bacterial origin in mammals, including humans. Thus the compounds of this invention can be administered in the form of a physiologically acceptable salt in a physiologically acceptable vehicle or carrier by injection or in the form of tablets or capsules, for example.

The preferred dosage range of the compositions of the present invention is about 5 mg/kg to about 15 mg/kg. The standard dosage for oral administration preferably ranges from 100 to 500 mg, and most preferably 250–500 mg. Reduced dosages for children and infants are preferred. Administration may be repeated during a 24-hour period.

Dosages for administration according to this invention may be compounded into oral dosage forms such as tablets, capsules, and the like. This is done by combining the compounds with conventional carriers and other excipients, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, solubilizers, lubricants, suspending agents, binders, tabletdisintegrating agents and the like may also be compounded with the compositions of the present invention. Active ingredients may be encapsulated with or without other carriers. In all cases, the proportion of active ingredients in these compositions, whether solid or liquid, will be at least sufficient to impart collagenase inhibitory activity in vivo after oral or parenteral administration.

The dosage requirements vary with the particular compositions employed, the route of administration, the severity of symptoms presented, and the particular subject being treated. Treatment will generally be initiated with small dosages less than the optimum dose of the compound. Throughout, the dosage may be increased until the optimum effect under the circumstances is reached. In general, the tangible embodiments of the invention are most desirably administered at a concentration that will generally afford effective results without causing any harmful or deleterious side effects. The dose will vary depending on these and other such factors which a person skilled in the art will recognize.

The ability of the compounds of the present invention to inhibit bacterial collagenase may be demonstrated by in vitro testing in an enzyme assay using collagenase produced by *Clostridium histolyticum*, for example.

The following examples show the preparation of representative compounds of the present invention. The compounds of the general formula I described above can be prepared by the following equation:

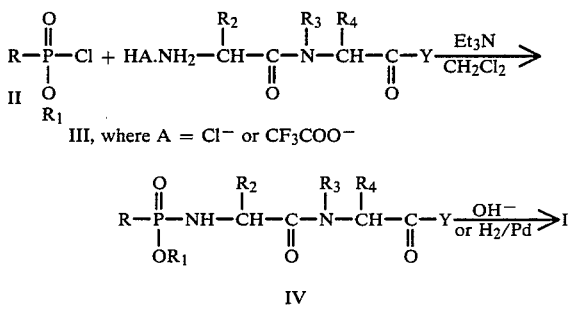

Compound (III) in a salt form is condensed in an inert solvent such as methylene chloride with phosphochloridate II in the presence of a base, such as triethylamine, to obtain ester IV. Specific hydrolysis or hydrogenolysis of ester IV affords the compound of formula I. Amino acids such as alanine or their derivatives such as alanine benzyl ester may be attached at Y at their α-amino group.

In the general formula I, $R_2$ and $R_4$ may be the side groups found on the 20 α-amino acids commonly found in proteins (also known as the standard amino acids). These side groups are well known in the art. See for example, FIGS. 4-2 to 4-4 in A. Lehninger, *Biochemistry* 2nd Ed., Worth Publishers, Inc. (1975), which figures are incorporated herein by reference. These side groups include straight and branched chain alkyl, hydrodroxy alkyl, carboxy alkyl, aralkyl, amino alkyl, carboxamide alkyl, mercapto alkyl, phenyl alkyl, hydroxy phenyl alkyl, guanidino alkyl, imidazoyl alkyl, indolyl alkyl, and pyrrolidinyl. The compounds of the present invention exhibit enhanced binding characteristics when $R_2$ and $R_4$ bear these side groups, thereby increasing their resemblance to a collagen or other protein fragment.

Also, specific compounds within the generic grouping of the present invention are also effective as inhibitors of other bacterial enzymes that degrade collagen, such as the elastase produced by the genus Pseudomonas. One example of such an elastase inhibitor is the amino acid derivative of the generic formula wherein R=ethyl, $R_1 = K^+$ or H, $R_2$=isoamyl, $R_3$=H, $R_4$=benzyl, and Y=$NH_2$.

Products of general formula I have asymmetric carbon atoms to which $R_2$, $R_4$ and $R_6$ are attached, when $R_2$, $R_4$ and $R_6$ are other than hydrogen. The compounds exist in diastereoisomeric forms or racemic mixtures thereof. All of these are within the scope of this invention, the L-isomer with respect to the carbon atom of the amino acids is generally preferred. The compounds of this invention form basic salts with various inorganic and organic bases which are also within the scope of this invention. Such salts include ammonium salts, alkali metal salts, alkaline earth metal salts, salts with organic bases, e.g. dicyclohexylamine, triethylamine and the like. The pharmaceutically acceptable salts are preferred, although other salts are also useful, e.g., in isolating or purifying the product.

Contemplated equivalents of the compounds employed in the compositions of this invention are those phosphorous-containing amino acid derivatives which are effective to inhibit bacterial collagenase. Because the inhibiting effect of the compound, rather than its exact chemical structure, is critical to this invention, it will be apparent to those skilled in the art that other

EXAMPLE 1

N$^\alpha$-(Dibenzylphosphoryl)-Glycyl-L-Proline Amide

To a fresh solution of dibenzylphosphochloridate prepared from 1.02 ml (4.6 mmoles) of dibenzyl phosphite by the method of Atherton et al., *J. Chem. Soc.*, 1948, 1106–1110, and 0.9 g (8.86 mmoles) of trifluoroacetate salt of glycyl-L-proline amide, 1.11 ml (0.8 mmoles) of triethylamine is added at 0° C. After 20 h at 0° C., the reaction mixture is diluted to 150 ml with methylene chloride and washed successively with 0.1N hydrochloric acid (2×25 ml), water (1×25 ml), 0.1 N sodium hydroxide (2×25 ml), water (2×30 ml) and saturated sodium chloride solution, dried over anhydrous sodium sulfate and evaporated yielding 1.4 g (84% yield) of N$^\alpha$-(dibenzylphosphoryl-glycyl-L-proline amide, melting point 91°–95° C. H$^1$-NMR (CDCl$_3$, TMS): $\delta$1.7–2.2 (m, 4H, Pro CH$_2\beta,\gamma$); 3.0–3.7 (m, 4H, Pro CH$_2\delta$, Gly CH$_2$); 4.1–4.6 (m, 2H, Pro CH$_\alpha$, P-NH-); 5.05 (d, 4H, PhCH$_2$); 6.3 (broad m, 1H, NH$_2$); 7.3 (m, 11H, Ph, NH$_2$). Mass spectrometry (methane chemical ionization (m/e): 432 (M+1), 450 (M+29), 472 (M+41).

EXAMPLE 2

N$^\alpha$-(Phosphoryl)-Glycyl-L-Proline Amide Dipotassium Salt

Hydrogen gas is bubbled for 1 h through a mixture of 0.43 g (1 mmole) of N$^\alpha$-(dibenzylphosphoryl)-glycyl-L-proline amide and 2 ml of 1.0N potassium hydroxide (2 mmoles) in 10 ml of 50% (v/v) aqueous tetrahydrofuran in the presence of 0.22 g of 10% palladium on carbon. After removal of catalyst by filtration, the filtrate is partially evaporated, frozen and lyophilized to give 0.3 g (91%) of the dipotassium salt of N$^\alpha$-phosphoryl-glycyl-L-proline amide. H$^1$-NMR (D$_2$O):$\delta$2.1 (m, 4H, Pro CH$_2\beta,\gamma$); 3.7 (m, 4H, Gly CH$_2$, Pro CH$_2\delta$),4.3(m, 1H, Pro CH$\alpha$).

EXAMPLE 3

N$^\alpha$-(Dibenzylphosphoryl)-Glycyl-L-Prolyl-L-Alanine Benzyl Ester

When benzyl-glycyl-L-prolyl-L-alaninate hydrochloride is substituted for glycyl-L-proline amide salt in Example 1, the identical process affords N$^\alpha$-(dibenzylphosphoryl)-glycyl-L-prolyl-L-alanine benzyl ester with yield 82%, melting point 77°–80° C. H$^1$NMR (CDCl$_3$) $\delta$1.35 (d, 3H, Ala CH$_3$); 1.8–2.2 (m, 4H, Pro CH$_2\beta,\gamma$) 3.2–3.8 (m, 4H, Pro CH$_2\gamma$, Gly CH$_2$) 3.9–4.3 (m, 2H, Ala CH, P-NH); 4.6 (m, 1H, Pro CH$_\alpha$), 5–5.3 (m, 2H, Ph CH$_2$); 7.35 (m, 16 H, Ph, Ala NH); MS (m/e): 594 (m+1).

EXAMPLE 4

N$^\alpha$-(Phosphoryl)-Glycyl-L-Prolyl-L-Alanine Tripotassium Salt

When N$^\alpha$-(dibenzylphosphoryl)-glycyl-L-prolyl-L-alanine benzyl ester is substituted for N$^\alpha$-(dibenzylphosphoryl)-glycyl-L-proline amide with 3 ml of 1.0N potassium hydroxide (3 mmoles) in Example 2 the identical process affords N$^\alpha$-phosphoryl-glycyl-L-prolyl-L-alanine tripotassium salt. H$^1$-NMR (D$_2$O) $\delta$1.61 d, 3H, Ala CH$_3$), 2.1 (m, 4H, Pro CH$_2\beta,\gamma$); 3.7 (m, 4H, Gly CH$_2$, Pro CH$_2\delta$); 4.2 (m, 1H, Ala CH$\alpha$) 4.45 (m, 1H, Pro CH$\alpha$).

EXAMPLE 5

N$^\alpha$-(O-Benzyl-P-Ethylphosphonyl)-Glycyl-L-Prolyl-L-Alanine Benzyl Ester When O-benzyl-P-ethylphosphochloridate, prepared from ethylphosphonate dibenzylester, by the method of Petrov et al, 1959, *J. Gen. Chem. USSR* 29, 1465–1467, is substituted for dibenzyl phosphochloridate in Example 3, the identical process affords N$^\alpha$-(O-benzyl-ethylphosphonyl)-glycyl-L-prolyl-L-alanine benzyl ester as an oil, with yield 65% after purification of the crude product by column chromatography [Silica gel, CHCl$_3$, (2) CH$_3$CN(2): i-PrOH (1)] H$^1$-NMR(CDCl$_3$ TMS) $\delta$0.8–2.2 (m, 8H, P-CH$_2$CH$_3$, Ala CH$_3$, Pro CH$_2\beta,\gamma$) 2.9–4.0 (m, 5H, Pro CH$_2\delta$, Gly CH$_2$ (d, 3.6 , P-NH);4.45 (m, 2H, Pro CH, Ala CH); 5.0 (m, 4H, PhCH$_2$); 7.3 (s, 10H, Ph) 7.45 (broad m, 1H, Ala, NH). MS (m/e:516 (M+1), 544 (M+29).

EXAMPLE 6

N$^\alpha$-(Ethylphosphonyl)-Glycyl-L-Prolyl-L-Alanine Dipotassium Salt

When N$^\alpha$(O-benzyl-P-ethylphosphonyl)-glycyl-L-prolyl-L-alanine benzyl ester is substituted for N$^\alpha$-(dibenzylphosphoryl)-glycyl-L-proline amide in Example 2 the identical process affords the titled compound with 100% yield. H$^1$-NMR (D$_2$O) $\delta$0.8–1.75 (m, 12H, P CH$_2$CH$_3$, Ala CH$_3$), 2.05 (m, 4H, Pro CH$_2\beta,\gamma$), 3.5 (m, 2H, Pro CH$_2\delta$) 3.65 (d, 2H, Gly CH$_2$), 4.15 (m, 1H, Ala CH), 4.45 (m, 1H, Pro CH$\alpha$).

EXAMPLE 7

N$^\alpha$-(O-Benzyl-P-iso-Amylphosphonyl)-Glycyl-L-Prolyl-L-Alanine Benzyl Ester When iso-amylphosphonate dibenzyl ester is substituted for ethylphosphonate dibenzyl ester in Example 5 the identical process affords N$^\alpha$-(O-benzyl-P-iso-amylphosphonyl)-glycyl-L-prolyl-L-alanine benzyl ester as an oil, with 40% yield after purification of crude product on column chromatography [silica gel, CHCl$_3$(3): CH$_3$CN(1): hexane (1): n-ProH(1)]. H$^1$-NMR(CDCl$_3$) $\delta$0.8 (d, 6H, i-Am CH$_3$); 1.25–2.2 (m, 12H, Ala CH$_3$, i-Am CH$_2\alpha,\beta$, CH$\gamma$, Pro CH$_2\beta,\gamma$); 3.15–3.85 (m, 5H, Pro CH$_2\delta$, Gly CH$_2$, P-NH); 4.5 (m, 2H, Pro CH$\alpha$, Ala CH$\alpha$); 5.0 (d, 2H, PhCH$_2$OP); 5.15 (s, 2H, PhCH$_2$OC); 7.35 (s, 11H, Ph, Ala NH). MS (m/e) 558 (M+1); 586 (M+29).

EXAMPLE 8

N$^\alpha$-(iso-Amylphosphonyl)-Glycyl-L-Prolyl-L-Alanine Dipotassium Salt

When N$^\alpha$-(O-benzyl-P-iso-amylphosphonyl)-glycyl-L-prolyl-L-alanine benzyl ester is substituted for N$^\alpha$-(ethylphosphonyl)-glycyl-L-prolyl-L-alanine benzyl ester in Example 6 the identical process affords the titled compound with 80% yield. H$^1$-NMR (D$_2$O) $\delta$0.75 (d, 6H, i-Am CH$_3$); 1.2–1.6 (m,5H, i-Am CH$_2\alpha,\beta$, CH$\gamma$); 1.95 (m, 4H, Pro CH$_2\beta,\gamma$); 3.3–3.68 (m, 5H, 4H, Pro CH$_2\delta$, Gly CH$_2$); 3.72–4.4 (m, 3H, Gly, CH$_2$, Pro CH$\alpha$).

EXAMPLE 9

N$^\alpha$-(O-Benzyl-P-n-Decylphosphonyl)-Glycyl-L-Prolyl-L-Alanine Benzyl Ester When n-decylphosphonate dibenzyl ester is substituted for iso-amylphosphonate dibenzyl ester in Example 7 the identical process affords the titled compound as an oil with 67% yield. H$^1$-NMR (CDCl$_3$) $\delta$0.08–2.3 (m, 28H, N-dec, Ala CH$_3$, Pro CH$_2\beta,\gamma$); 3.0–4.0 (m, 5H, Pro CH$_2\delta$, Gly CH$_2$, P-NH) 4.4–4.8 (m 2, H, Ala CH, Pro CH); 5.05 (d, 2H, PhCH$_2$OP) 5.2 (s, 2H, PhCH$_2$OC); 7.3 (s, 10H, Ph); 7.5 (broad s, 1H, Ala NH). MS (m/e) 6.28 (M+1), 656 (M+29).

EXAMPLE 10

N$^\alpha$-(n-Decylphosphonyl)-Glycyl-L-Prolyl-L-Alanine Dipotassium Salt

When N$^\alpha$-(O-Benzyl-P-n-decylphosphonyl)-glycyl-L-prolyl-L-alanine benzyl ester is substituted for N$^\alpha$-(O-benzyl-P-iso-amylphosphonyl)-glycyl-L-prolyl-L-alanine benzyl ester in Example 8 the identical process affords the titled compound with 89% yield. H$^1$-NMR (D$_2$O) $\delta$0.75–1.65 (m, 24H, n-decyl, Ala CH$_3$); 1.95 (m, 4H, Pro CH$_2\beta,\gamma$); 3.45 (m, 2H, Pro CH$_2\delta$); 4.0 (m, 1H, Ala CH$\alpha$); 4.25 (m, 1H, Pro CH$\alpha$).

EXAMPLE 11

N$^\alpha$-(O-Benzyl-P-iso-Amylphosphonyl)-Glycyl-Glycyl-L-Proline Benzyl Ester

When benzyl glycyl-glycyl-L-prolinate hydrochloride is subsituted for benzyl glycyl-L-prolyl-L-alaninate hydrochloride in Example 7 the identical process affords the titled compound as an oil with 33% yield. H$^1$-NMR (CDCl$_3$,TMS): $\delta$0.8 (d, 6H, i-Am CH$_3$); 1.3–2.2 (m, 9H, i-Am CH$_2\alpha,\beta$, CH$\gamma$, Pro CH$_2\beta,\gamma$);3.3–4.5 (m, 8H, pro CH$_2\delta$, CH$\alpha$, Gly CH$_2$, P-NH); 5.0–5.3 (m, 4H, Ph CH$_2$); 7.3 (s, 10H, Ph) 7.6 (broad m, 1H, Gly NH). MS (m/e): 544 (M+1); 572 (M+29); 584 (M+41).

EXAMPLE 12

N$^\alpha$-(iso-Amylphosphonyl)-Glycyl-Glycyl-L-Proline Dipotassium Salt

When N$^\alpha$-(o-benzyl-P-iso-amylphosphonyl)-glycyl-glycyl-L-proline benzyl ester is substituted for N$^\alpha$-(O-benzyl-P-n-decylphosphonyl)-glycyl-L-prolyl-L-alanine benzyl ester in Example 10 the identical process affords the title compound with 80% yield. H$^1$-NMR (D$_2$O) $\delta$0.75 (d, 6H, i-Am CH$_3$); 1.2–1.6 (m, 5H, i-Am CH$_2\alpha,\beta$, CH$\gamma$); 1.95 (m, 4H, Pro CH$_2\beta,\gamma$); 3.3–3.68 (m, 4H, Pro CH$_2\delta$, Gly CH$_2$); 3.72–4.4 (m, 3H, Gly CH$_2$, Pro CH$\alpha$).

EXAMPLE 13

In a conventional manner, fill gelatin capsules with, or prepare compressed tablets containing 150, 350 or 500 mg of N$^\alpha$-(Dibenzylphosphoryl)-Glycyl-L-Prolyl-L-Alanine benzyl ester per capsule or tablet. Administer one to two capsules or tablets three or four times daily to an adult in order to treat the effects of a Clostridium infection.

EXAMPLE 14

Prepare an alcoholic (8½%) mint-flavored and sweetened solution of 500, 750 or 1000 mg of N$^\alpha$-(Ethylphosphonyl)-Glycyl-L-Prolyl-L-Alanine Dipotassium Salt per fluid ounce (30 ml). Administer ⅔ fluid ounce up to six times daily, or one fluid ounce up to four times daily, every four to six hours for the treatment of bacterial tissue infection.

EXAMPLE 15

The collagenase inhibitors of the present invention may also be useful as in vitro reagents in the production of unicellular suspensions from tissue samples.

Under sterile conditions, excise the distal ⅔ of a raccoon tail. With a sterile razor blade scrape the surface of the tail in order to remove hairs present thereon. Next place the tail portion in a solution of clorox or other bleach for approximately 30 minutes in order to dissolve any remaining hair or surface contaminants. After removing the tail from this bath, rinse three times serially in sterile distilled water. Then dissect away the epidermal portion of the tissue sample, and with forceps and a sterile scalpel, tease away remaining tissue present. This should result in approximately 5 to 15 grams of raccoon tail tissue.

In a sterile petri dish, using scissors and forceps, gently mince the tissue into small fragments. Then with a magnetic stirring bar and stirrer apparatus place the minced tissue in a volume of approximately 20 ml of sterile Ringers lactate, and add 10 ml of 0.05% collagenase solution. Allow the stir bar to rotate for approximately 1 hour, or until the tissue sample is sufficiently disaggregated. Filter the suspension through sterile gauze and isolate further clumps by low speed centrifugation.

To the supernatant add 5.0 ml of 0.1% collagenase inhibitor as disclosed in the present invention, mix thoroughly, and then pellet the cells by higher speed centrifugation. Wash by resuspending the cell pellet three times with serial recentrifugations, resuspend in sterile RPMI 1640 culture solution and add aliquots of appropriate volume to cell culturing vessels and incubate.

EXAMPLE 16

The bacterial collagense inhibitors of the present invention are also useful in the formation of affinity chromatography columns to bind collagenase. Affinity columns using collagenase inhibitors as a ligand may be prepared in the method of Komiyama et al., "Inhibitory Effects of Phosphoramidon on Neutral Metalloendopeptidases and its Application on Affinity Chromatography", 65(1)352: 357 (1975). One gram of AH-sepharose 4B is washed with 0.5M NaCl and with water is mixed with 77 mg of 1-ethyl-3(3-dimethylaminopropyl) carbodiimide hydrochloride and 50 mg of N$^\alpha$-(P-iso-amylphosphonyl)-Glycyl-L-Prolyl-L-alanine in 5.0 ml of aqueous solution at pH 5.0. This preparation is left at room temperature with gentle stirring for one day. After reaction, the gel is packed into a small column (1×5 cm), and washed successively with 10 ml of each of the following solutions: 1M NaCl, 0.1M tris-HCl containing 1M NaCl, pH 8.0, 50 mM formic acid containing 1M NaCl, pH 3.0; 0.1M tris-HCl containing 1M NaCl, pH 8.0; 50 mM tris-HCl, pH 8.0; and then equilibrated with 10 mM tris-HCl containing 5 mM CaCl$_2$, pH 7.0. Under these conditions about 10 micromoles of the inhibitor is coupled with 1 ml of swelled gel. Elutions of bacterial collagenase from the column are performed in a conventional manner.

From the foregoing description, one skilled in the art can easily ascertain the essential characteristics of this invention, and without departing from the spirit and scope thereof, can make various changes and modifications of the invention to adapt it to various usages and conditions. The foregoing preferred specific embodiments are, therefore, to be construed as merely illustrative and not limitative of the disclosure in any way whatsoever.

We claim:

1. A method for inhibiting bacterial collagenase in vivo wherein the bacteria are selected from the group consisting of Clostridium and Pseudomonas, which comprises administering to a human being a collagenase inhibiting effective amount of a pharmaceutical composition including a compound of the formula:

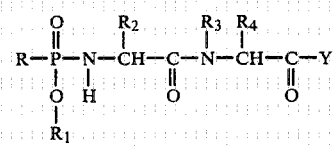

wherein R is alkyl, aralkyl, aryl, alkoxy, aryloxy, hydroxy or pharamceutically acceptable salts thereof; $R_1$ is hydrogen, alkali metal, lower alkyl, phenyl lower alkyl, or phenyl, or substituted phenyl wherein the substituent is halo, lower alkoxy or lower alkyl or nitro or carboxy or cyano, and pharmaceutically acceptable salts thereof; $R_2$, $R_3$ and $R_4$ are hydrogen or alkyl; $R_2$ and $R_4$ are selected from the group consisting of straight and branched chain alkyl, hydroxy alkyl, carboxy alkyl, aralkyl, amino alkyl, carboxamide alkyl, mercapto alkyl, phenyl alkyl, hydroxy phenyl alkyl, guanidino alkyl, imidazoyl alkyl, indolyl alkyl, and pyrrolidinyl; $R_3$ and $R_4$ may be connected together to form an alkylene bridge of from 2 to 4 carbon atoms; Y is alkoxy, aryloxy, primary amide, alanine benzyl ester or

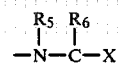

where $R_5$ and $R_6$ is hydrogen or alkyl; $R_5$ and $R_6$ may be connected together to form an alkylene bridge of from 2 to 4 carbon atoms; and X is hydroxyl or pharmaceutically acceptable salts thereof, in admixture with a pharmaceutically acceptable carrier.

2. A method according to claim 1, wherein the composition is adapted for oral ingestion and is administered orally.

3. A method according to claim 1, wherein the composition is adapted for parenteral administration and is administered parenterally.

4. A method according to claim 1, in the form of a tablet or capsule.

5. A method according to claim 1, in the form of an aqueous solution.

6. A method of inhibiting the action of a bacterial collagenase in vitro wherein the bacteria are selected from the group consisting of clostridium and Pseudomonas, by allowing the collagenase to react with an inhibition-effective amount of a compound of the formula:

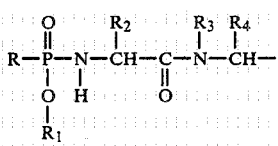

wherein R is alkyl, aralkyl, aryl, alkoxy, aryloxy, hydroxy or pharmaceutically acceptable salts thereof; $R_1$ is hydrogen, alkali metal, lower alkyl, phenyl lower alkyl, or phenyl, or substituted phenyl wherein the substituent is halo, lower alkoxy or lower alkyl or nitro or carboxy or cyano, and pharmaceutically acceptable salts thereof; $R_2$, $R_3$ and $R_4$ are hydrogen or alkyl; $R_2$ and $R_4$ are selected from the group consisting of straight and branched chain alkyl, hydroxy alkyl, carboxy alkyl, aralkyl, amino alkyl, carboxamide alkyl, mercapto alkyl, phenyl alkyl, hydroxy phenyl alkyl, guanidino alkyl, imidazoyl alkyl, indolyl alkyl, and pyrrolidinyl; $R_3$ and $R_4$ may be connected together to form an alkylene bridge of from 2 to 4 carbon atoms; Y is alkoxy, aryloxy, primary amide, alanine benzyl ester or

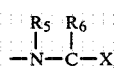

where $R_5$ and $R_6$ is hydrogen or alkyl; $R_5$ and $R_6$ may be connected together to form an alkylene bridge of from 2 to 4 carbon atoms; and X is hydroxyl or pharmaceutically acceptable salts thereof, in admixture with a pharmaceutically acceptable carrier in an appropriate solution.

7. The method of claim 6, wherein R=ethyl, $R_1$=K$^+$ or H, $R_2$=isoamyl, $R_3$=H, $R_4$=benzyl, and Y=NH$_2$.

8. The method of claim 1, wherein R=isoamyl, $R_1$=K$^+$ or H, $R_2$=H, $R_3$+$R_4$=—CH$_2$CH$_2$CH$_2$—, and Y=Alanine.

9. The method of claim 1, wherein R=ethyl, $R_1$=K$^+$ or H, $R_2$=H, $R_3$+$R_4$=—CH$_2$CH$_2$CH$_2$—, and Y=Alanine.

10. The method of claim 1, wherein R=isoamyl, $R_1$=benzyl, $R_2$=H, $R_3$+$R_4$=—CH$_2$CH$_2$CH$_2$—, and Y=Alanine benzyl ester.

11. The method of claim 1, wherein R=ethyl, $R_1$=benzyl, $R_2$=H, $R_3$+$R_4$=—CH$_2$CH$_2$CH$_2$-, and Y=Alanine benzyl ester.

* * * * *